United States Patent [19]

Keith

[11] Patent Number: 5,580,554
[45] Date of Patent: Dec. 3, 1996

[54] METHODS OF TREATING PREECLAMPSIA

[75] Inventor: James C. Keith, Andover, Mass.

[73] Assignees: Genetics Institute, Inc., Cambridge, Mass.; Virginia Polytechnic Institute and State University, Blacksburg, Va.

[21] Appl. No.: 409,386

[22] Filed: Mar. 23, 1995

Related U.S. Application Data

[63] Continuation-in-part of Ser. No. 212,446, Mar. 10, 1994.

[51] Int. Cl.$^6$ .................................................. A61K 45/05
[52] U.S. Cl. ...................... 424/85.1; 424/85.2; 530/351; 530/399
[58] Field of Search ................................ 424/85.1, 85.2; 530/351, 399

[56] References Cited

U.S. PATENT DOCUMENTS 4,868,119  9/1989  Clark et al. .......................... 435/240.2
4,879,227  11/1989  Clark et al. ............................. 435/70

OTHER PUBLICATIONS

Schrocksnadel et al., Pteridines, vol. 4, pp. 144–148, 1993.
Koenig et al., Am J. Obstet, Gynecol., vol. 165, pp. 467–473, 1991.
Gessler et al. Blood, vol 82(10), pp. 3177–3182, 1993.
Stark, Brit. J. Obstet. Gynecol., vol. 100, pp. 105–109, 1993.
Tabibzadeh, Endocrine Reviews 12:272–290 (1991).
Pollard et al., Nature 330:484–486 (1987).
Uzumaki et al., PNAS USA 86:9323–9326 (1989).
Kanzaki et al., Human Reprod. 7:563–567 (1992).
Meekins et al., Clin. Exp. Immunol., vol. 98, pp. 110–114 (1994).
Vince et al., Brit. J. Obstet. Gynecol., vol. 102, pp. 20–25 (1995).
Keith et al., J. Perinatology, vol. XIII, No. 5, pp. 417–419 (1993).
Greer et al., Obstet Gynecol., vol. 84, No. 6, pp. 937–940 (1994).
Chegini et al., *Growth Factors and the Ovary*, pp. 213–220 (Hirschfield ed.) Plenum Press, N.Y. (1988).
Daiter et al., J. Clin. Encocrinol. Metab. 74:850–858 (1992).
Li et al., J. Clin. Endocrinol. Metab. 74:184–191 (1992).
Jäättelä et al., Lab. Invest. 58:48–52 (1988).
Guilbert et al., J. Leukocyte Biol. 54:65–72 (1993).
Pijnenborg, *Trophoblast Research*, pp. 33–47 (Denker and Aplin, eds) Plenum Press, N.Y. (1990).
Schäfer et al., *J. Perinat. Med.* 20:233–240 (1992).
Ault et al., Blood, vol. 84(10), Suppl 1, p. 276a, 1994.
Loke et al., J. Reproduc. Immunol. 22:33–45 (1992).
Khong et al., Br. J. Obstet. Gynecol. 93:1049–1059 (1986).
Robertson et al., Am. J. Obstet. Gynecol. 155:401–412 (1986).
Yong et al., Blood 80:2897–2902 (1992).
Kupfermine et al., Am J Obstet Gynecol 170:152–9 (1994).
Schrücksnadel et al., Geburtshilfe Fraucnheilkd 52(10):592–5 (1992) Medline: 93194034.

*Primary Examiner*—Chhaya D. Sayala
*Attorney, Agent, or Firm*—Steven R. Lazar; Thomas J. DesRosier

[57] ABSTRACT

Methods are provided for the diagnosis and treatment of patients with increased risk of gestational hypertension or preeclampsia. The methods involve measuring serum M-CSF levels, and administration of M-CSF.

7 Claims, 1 Drawing Sheet

METHODS OF TREATING PREECLAMPSIA

CROSS REFERENCE TO RELATED APPLICATION

This application is a continuation-in-part of Ser. No. 08/212,446, filed Mar. 10, 1994.

FIELD OF THE INVENTION

This invention relates to the use of cytokines, particularly M-CSF, for the diagnosis and treatment of preeclampsia.

BACKGROUND OF THE INVENTION

Preeclampsia is a major cause of maternal and fetal mortality and morbidity, and is a disease unique to human beings during pregnancy. Recent evidence has indicated that preeclampsia is characterized by placental maladaptation and body-wide endothelial cell injury. Failure of trophoblastic invasion into myometrial segments of maternal spiral arteries and the production of cytotoxic mediators which cause systemic endothelial damage also seem to be implicated.

Trophoblasts are a unique cell type in that they share characteristics of both normal and neoplastic tissue. During normal development, like neoplastic cells, human trophoblasts invade through the extracellular matrix into the myometrial portion of spiral arteries. However, unlike neoplastic cells which endlessly invade and finally spread to other organs, the invasive properties of the trophoblasts are eventually brought under control, further cell differentiation proceeds and cell senescence occurs. In normal gestation, trophoblasts convert spiral arteries into uteroplacental arteries by the above process. Pijnenborg et al., in *Trophoblast Research* (Denker and Aplin, eds.) Plenum Press, New York, p. 33 (1990). Uteroplacental arteries then dilate approximately 30-fold as large as the spiral arteries. Resulting hemodynamic changes enable the placental bed to satisfy the increased demand for oxygen from the fetus during the latter stages of gestation. In preeclamptic women, however, spiral arteries are not properly converted into uteroplacental arteries due to the failure of the second wave of trophoblastic migration into the myometrium at the beginning of the second trimester. Khong et al., *Br. J. Obstet. Gynecol.*, 93:1049–1059 (1986). As a result, preeclamptic women typically demonstrate a high-resistance, high-pressure, and low-flow state with intact, non-dilated spiral arteries, Robertson et al., *Am. J. Obstet. Gynecol.*, 155:401–412 (1986), and demonstrate a wide variety of clinical syndromes. Therefore, abnormal behavior of the fetus-derived trophoblast appears to be a central aspect of the disease.

Cytokines provide an important communication system in coordinating immune and inflammatory responses. Among the cytokines are a number of colony stimulating factors (CSFs), which are named for their major target cells, including granulocyte (G-CSF), granulocyte-macrophage (GM-CSF) and macrophage (M-CSF, also known as CSF-1) colony stimulating factors. Other cytokines include the interleukins, including IL-1 through IL-13, which are known to possess varying activities including being involved in hematopoiesis, and providing defenses against pathogenic infections.

Cytokines are produced in the uterus and placenta during normal pregnancy. Tabizadeh, *Endocrine Reviews*, 12:272–290 (1991). In rats, it has been observed that M-CSF is secreted by uterine gland cells, and the levels increased approximately one thousand-fold in the first few days of pregnancy, with the novel receptor present on invasive trophoblast cells. Pollard et al., *Nature*, 330:484–486 (1987); Uzumaki et al., *PNAS, USA*, 86:9323–9326 (1989). In humans, the expression and localization of mRNA for M-CSF have been demonstrated in mesenchymal cells of the chorionic villous stroma, particularly in cytotrophoblasts lining the villous core and in the cytotrophoblastic core in the first trimester; in villous mesenchymal cells in the second trimester; and in cells lining the villous vessels in the third trimester. Kanazaki et al., *Human Reprod.*, 7:563–567 (1992); Daiter et al., *J. Clin. Endocrinol. Metab.* 74:850–858 (1992). Circulating levels of macrophage M-CSF during pregnancy are also higher than those of non-pregnant women. Yong et al., *Blood*, 180:2897–2902 (1992).

Other cytokines have been identified in placenta and/or uterus. TNF-α is present in human amniotic fluids and supernatants of placental and decidual tissues. Jaattela et al., *Lab. Invest.* 58:48–52 (1988). Trophoblast derived TNFα induces release of human chorionic gonadotropin (hCG) using IL-6 and IL-6 receptor-dependent systems in normal human trophoblasts. Ying et al., *J. Clin. Endocrinol. Metab.*, 74:184–191 (1992). Conversely, hCG and human placental lactogen (hPL) increase the expression of TNFα. Schafer et al., *J. Perinat. Med.*, 20:233–240 (1992).

SUMMARY OF THE INVENTION

Accordingly, the present invention provides methods of detecting, preventing and/or treating preeclampsia by measuring and, if necessary, increasing levels of biological factors which are normally present in the placenta and/or uterus, but are absent, or present in reduced concentrations, in preeclamptic women. Preferred biological factors include circulating cytokines, particularly CSFs, such as M-CSF, interleukins, such as IL-11, and growth factors, such as TNF-α. The most preferred growth factor for the methods of the present invention is M-CSF.

In one particular embodiment, the present invention comprises a method of diagnosing the increased risk of gestational hypertension or preeclampsia comprising measuring serum M-CSF levels in a patient suffering from, or who may be susceptible to, preeclampsia or gestational hypertension ("GH"). In a preferred embodiment, serum M-CSF levels are measured in a pregnant woman at about 14 to 16 weeks gestation. These serum M-CSF levels are compared to the serum level of M-CSF in women with normal pregnancies. As demonstrated later herein, the serum M-CSF levels are correlated with the occurrence of preeclampsia or gestational hypertension (GH) at final pregnancy outcome; hence, the present invention is useful in order to gain an accurate prediction of increased risk of incidence of preeclampsia and/or GH at final pregnancy outcome. This information may be used to identify those women who may benefit from treatment with M-CSF.

The inventor has discovered that serum TNF-α levels are decreased during the early stages of preeclamptic pregnancy, and therefore may be of additional value in diagnosing and/or treating the increased risk of gestational hypertension or preeclampsiain early stages. During later stages of preeclamptic pregancy, TNF-α levels become increased.

In another embodiment, the present invention comprises a method of treating a woman suffering from, or who may be susceptible to, preeclampsia or GH with M-CSF. In one embodiment, the present invention comprises administering therapeutically effective dosages of a cytokine, such as M-CSF, to a patient, usually a pregnant woman who is determined to be susceptible to, or who suffers from, preeclampsia or GH. In addition to M-CSF, the patient may be treated with one or more other biological factors, such as IL-11.

In another embodiment, the present invention comprises the administration of cells which have been treated with, or transfected with, a gene encoding for expression of one or more cytokines, particularly CSFs, and more particularly M-CSF. In a preferred embodiment, the cells used are trophoblasts which have been removed from the patient, treated with, or transfected with, a gene encoding for the cytokine(s) in order to render the trophoblasts able to express greater amounts of the cytokine(s), and then administered to the patient, usually a pregnant woman who is determined to be susceptible to, or who suffers from, preeclampsia. Vectors and genes useful for preparing the transfected cells are described in U.S. Pat. Nos. 4,868,119 and 4,879,227, the disclosures of which are hereby incorporated by reference.

DETAILED DESCRIPTION OF THE INVENTION

Figure 1:
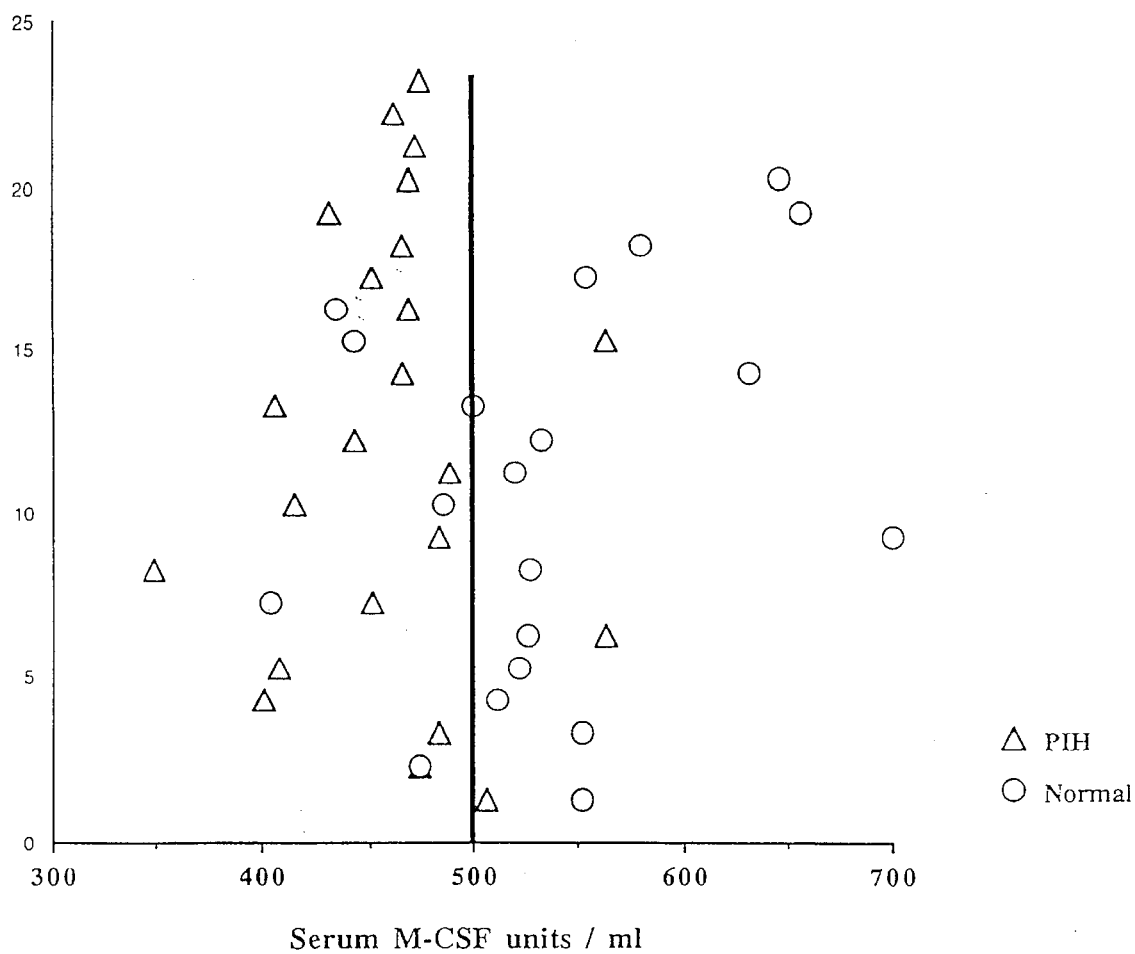
FIG. 1 is a diagram of the relationship between serum M-CSF levels measured at 16 weeks gestation and final pregnancy outcome (Δ=patient with GH ("PIH"); ☉=patient with normal pregnancy).

The biological factors useful for the present invention include those which are normally produced in the local environment of proliferating trophoblasts. Among the biological factors useful for the present invention are cytokines, particularly the colony stimulating factors, such as G-CSF, GM-CSF, and M-CSF and interleukins, such as IL-1 through IL-13. Other cytokines useful for administration in the methods of the present invention include tumor necrosis factor, especially TNF-α, interferons, and growth factors, such as transforming growth factor β, IGF, and FGF. Other biological factors useful for administration in the present invention include fatty acid metabolites, such as prostacyclin, leukotrienes and PAF. The preferred biological factors are M-CSF alone or in combination with GM-CSF, IL-11 or other biological factors.

The present invention also includes methods of determining the biological factors which are most appropriate for administration to a patient. In determining the appropriate biological factors to be administered to a patient, the physician may measure the levels of biological factors present in the placenta and/or uterus. Those factors which are present in reduced levels compared to normal pregnancy may be considered as appropriate factors for administration to a patient.

In a particular embodiment of the present invention, pregnant women may be diagnosed for increased risk of gestation hypertension or preeclampsia by measuring serum M-CSF levels during the first trimester of pregnancy [approximately 1 to 14 weeks]. It is preferred that the M-CSF levels be measured at least twice during this period, preferably including a measurement at about 14 to 16 weeks. If the M-CSF levels are significantly below normal, a course of treatment via administration of M-CSF may be used. In general, levels of 500 units/ml M-CSF or above are considered normal. However, M-CSF levels of about 500 to about 600 units/ml M-CSF may be suspect, and further monitoring, in the form of assay for TNF-α, or additional measurements of M-CSF, may be appropriate. A unit of M-CSF is equivalent to approximately 12 picogram M-CSF. Thus, units may be measured by direct assay of the amount of M-CSF present [the exact ng/ml of M-CSF present in serum], or by bioassay [level of activity of the M-CSF in the serum compared to that of 12 picograms of M-CSF]. If the patient's serum M-CSF level is below about 500 units/ml, the patient may be diagnosed as being at increased risk of suffering gestational hypertension and/or preeclampsia. A course of treatment for management of hypertension may be appropriate.

If additional monitoring is called for, such monitoring may be accomplished by measuring the serum biological activity level of TNF-α in the patient. Serum biological activity levels of approximately 40 units/ml or more of TNF-α are generally considered normal. See Keith et al., *J. Perinatology*, 13:417–418 (1993), and Keith et al. *Hypertension and Pregnancy* (1995) 14:81–90, the disclosure of both of these articles are hereby incorporated by reference. If the serum M-CSF level is below normal, or suspect, and serum TNF-α levels are also below normal, the patient may be diagnosed to be at increased risk of suffering gestational hypertension and preeclampsia.

In another embodiment of the present invention, a patient with increased risk of gestational hypertension or preeclampsia is treated via administration of M-CSF. Preferably, treatment with M-CSF begins late in the first trimester, at about 14 to about 16 weeks, or early in the second trimester, at about 16 to about 18 weeks, and may continue until measured serum M-CSF levels are elevated to within normal levels. Preferably, treatment with M-CSF is not continued beyond about 30 weeks of gestation. For the purposes of the present invention, normal serum M-CSF levels are defined as those levels typical for pregnant women who do not suffer from preeclampsia or gestational hypertension, generally at least approximately 500 units/ml. [500 units/ml≊6 nanogram/ml]. Preferably, treatment with M-CSF is discontinued after M-CSF levels are within normal levels, and before any adverse effects of M-CSF administration are observed.

In a preferred embodiment, M-CSF may be administered together with, or prior to, administration of IL-11. Recently, Ireland et al. (Blood 84:267a (1994)) reported that interleukin-11 (IL-11) was produced by placental fibroblasts, and that it appeared to be involved in trophoblast differentiation and placentation. In normal pregnancy plasma volume is typically in an expanded physiologic state, but preeclampsia is a decreased plasma volume state. IL-11 may help increase plasma volume (Ault et al., Blood 84:276a (1994)) and may modulate production of TNF-α, which becomes elevated during late pregnancy in cases of preeclampsia. Keith et al., (1993), supra, and Keith et al. (1995), supra. Therefore, treatment with M-CSF beginning prior to treatment with IL-11 may prove synergistic. Early treatment with M-CSF [beginning in the first trimester and continuing approximately until normal M-CSF levels are achieved] and later treatment with IL-11 [starting in the second trimester, preferably at approximately 18 to 22 weeks of pregnancy and continuing until about 36 weeks of pregnancy] may produce optimal resolution of preeclampsia.

In the methods of the present invention, M-CSF and/or other factors may be administered through any known means. Administration should be systemic, e.g., parenteral. The preferred mode of administration is subcutaneous, preferably not more than 1× daily. The therapeutically effective amount should be insufficient to cause a systemic toxic reaction, but sufficient to elicit the desired therapeutic response. The actual dosing regimen for such formulations will be determined by the attending physician considering various factors which modify the action of drugs, for example, the condition, body weight, sex and diet of the patient, time of administration, and the degree of onset of the disease.

In general, a therapeutically effective dose of M-CSF, i.e., an amount sufficient to increase the serum M-CSF level to within normal ranges, is expected to be in the range of about 1–200 µg/kg/day or more preferably in the range of about 5–150 µg/kg/day. The methods of the present invention may involve a series of administrations of the pharmaceutical compositions. Such a series may take place over a period of about 7 to about 21 days. One or more series may be administered.

In a preferred embodiment wherein IL-11 is administered, a therapeutically effective dose of IL-11 is expected to be in the range of about 1–100 µg/kg/day or more preferably in the range of about 1–50 µg/kg/day. The IL-11 is preferably administered subcutaneously.

Generally, administration will be initiated at the low end of the dosing range initially, and the dose will be increased over a preselected time course until a positive effect is observed. Subsequently, incremental increases in dosage will be made limiting such incremental increases to such levels that produce a corresponding increase in effect, while taking into account any adverse affects that may appear. The duration and frequency of intravenous or sucutaneous therapy using the method of the present invention will vary, depending on the severity of the disease, or growth factor depletion being treated and the condition and potential idiosyncratic response of each individual patient. It is contemplated that the duration of each intravenous application of M-CSF will be in the range of 12 to 24 hours of continuous administration. Ultimately, the attending physician will decide on the appropriate duration of therapy using the method of the present invention.

For gene therapy, a preferred cell type for administration of the cytokines in the present invention are trophoblasts. As discussed above, trophoblasts are a unique cell type which are active in the uterus and/or placenta during pregnancy.

EXAMPLES

EXAMPLE 1

Trophoblast Cell Culture

Placental specimens are obtained from consenting normal pregnant women and preeclamptic women at the time of delivery. Primary cell cultures of trophoblasts isolated from human placenta of normal and preeclamptic pregnancies are established according to a modified technique of Kliman et al., *Endocrinology*, 118:1567–1582 (1986), as described herein.

(Day 1) Placenta is obtained and maintained with aseptic technique and rinsed with cold PBS. Several sections (20 grams) of placenta taken from the maternal side of the placenta is placed in a sterile petri dish and washed with cold sterile PBS to rinse off blood clots. Trophoblast cells are separated from connective tissue materials using a scalpel. The cells are covered with the petri dish lid, weighed, and added to 50 ml of trypsin solution.

(Day 2) After overnight at 4° C., the cells are mixed with 0.01% DNase I (dry powder) with trypsin, and incubated in water bath at 37° C. for 15 minutes. DMEM with fetal calf serum (FCS) 20% 10 ml medium per 50 ml solution is added and left for 1 minute. The solution is filtered (20µ) and then poured into sterile Gibco flasks. The cells are suspended by shaking the solution. Finally, the cells are centrifuged over a continuous Percoll gradient.

The trophoblast cells are cultured in DMEM supplemented with 20% FCS on fibronectin-coated plastics, or in endothelial cell growth medium (Gibco) after using vitronectin-containing endothelial cell plating medium (Gibco) to encourage cell attachment. Since these cells show very little proliferative activity, subculturing is not feasible, but freezing of freshly isolated trophoblastic cells can be performed. Freezing of some of the cells allows multiple experiments on cells obtained under similar conditions.

JEG-3 choriocarcinoma cell lines may also be used as models of first trimester trophoblast effects. JEG-3 choriocarcinoma cell lines are cultured according to standard cell culture techniques, using DMEM supplemented with 20% FCS in Falcon flasks or Nunc microtiter plates.

After the wells of the Nunc microtiter plates are washed with minimum essential medium, the medium is changed to culture medium supplemented with M-CSF or appropriate vehicles. The cells are incubated for 24, 48 or 72 hrs before the culture media are removed and centrifuged at 600 g for 10 minutes to eliminate cell debris. The supernatants are stored at −70° C. until assayed for cytokines and fatty acid metabolites. The plates are fixed with 4% paraformaldehyde in PBS and stained for evaluation of cell morphology and number.

The results of this histological observation are reported in Example 3.

EXAMPLE 2

Measurement of Cytokines and Fatty Acid Metabolites

A. ELISA for Cytokines: Cytokines are measured with commercially available, enzyme-linked immunosorbent assay kits (ELISA)(Genzyme Corporation, Cambridge, Mass.). The assay is a triple antibody sandwich using a monoclonal anti-GM-CSF, -G-CSF, -M-CSF, or -TNFα biotinylated goat anti-rabbit immunoglobulin with streptavidin-peroxidase, and 0-phenylenediamine as the chromogen.

B. Bioassay for TNFα: The L929 mouse fibrosarcoma cell cytotoxicity assay for TNFα bioactivity is performed as follows in 96 well microtiter plates in triplicates. L929 target cells, washed and resuspended in DMEM+10% FCS, are placed at a density of $1.0 \times 10^5$ cells/ml and 250 µl/well. After allowing the cells to attach to the well bottoms overnight, the media are removed and replaced with fresh identical media containing test samples. After 16–18 hrs incubation at 37° C., 40 µl of a 2.5 mg/ml solution of (3-[4,5-dimethylthiazol-2-y]-2,5-diphenyltetrazolium bromide)(MTT)(Sigma Chemical Co., St. Louis, Mo.) in PBS is added to each well. After incubation with MTT for two hours at 37° C., the supernatants are removed and the formazan crystals (reaction products) are solubilized with 100 µl of Sorenson's Glycine Buffer. Plates are then read in a spectrophotometer at 550 nm using a microplate reader. FCS controls should give an approximate absorbance of 0.650–0.900. Cytotoxicity is expressed as % of FCS control, subtracted from 1 to yield the cytotoxic index. The specificity of the assay is confirmed by neutralization of cytotoxicity with anti-TNFα antibodies.

C. Bioassay for GM-CSF and M-CSF: FDCP-G cells and doubling dilutions of samples for assay or recombinant GM-CSF and M-CSF as standards are incubated in triplicates in microtiter plates. After 24 hrs preincubation, [$^3$H] methyl thymidine is added (0.5 µCi/well). 16–18 hrs later, cells are harvested and radioactive incorporation measured as counts per min (cpm). To neutralize GM-CSF activity, 160 µl of neutralizing antibody to GM-CSF is incubated at 4 hrs at 37° C. with 160 µl of 5637 CM medium conditioned by incubation with trophoblast tissue, or RPMI/BSA as a control. For recombinant GM-CSF, 160 µl of antibody (10 µg/ml) is incubated with 160 µl of 2.5 ng/ml rGM-CSF.

EXAMPLE 3

Evaluation of Trophoblast Cells

A. Cytological Examination: Cells are grown on plastic coverslips with and without added cytokines or anti-cytokine antibodies. At 24, 48 and 72 hrs of incubation, cells are fixed with 4% paraformaldehyde in PBS (pH 7.4), stained with toluidine blue, and examined by light microscope, including assessment of the degree of giant cell formation. Photomicroscopy may be performed and evaluated.

B. Proliferation Assays:

1) MTT Assay [Described in Example 2B]: Proliferation expressed as % FCS.

2) [$^3$H] Thymidine Incorporation: Trophoblast cell lines are washed twice with PBS and culture medium is reconstituted. The selected cytokines or antibodies are added to the wells. [$^3$H] thymidine at a concentration of 1 µCi per well is added at the same time point as test compounds, and the cultures are incubated for 24, 48 or 72 hrs. Proliferative response is evaluated from the beta counts of cells harvested at the end of the incubation period with a cell harvester.

C. Hormone Content Analysis (hCG): The secretion of hCG into the media of each culture is identified with a microparticle enzyme immunoassay (Abbott Laboratories, Abbott Park, Ill.) for β-subunit chains. Briefly, diluted samples of conditioned media are treated with anti-hCG antibodies conjugated with alkaline phosphatase. This enzyme-antibody-antigen complex is then incubated with anti-hCG-coated microparticles, and an aliquot of this mixture is transferred to a glass fiber matrix. The matrix is then washed to remove unbound material and the substrate; 4-methylumbelliferyl phosphate is added, and the resulting fluorescence is measured.

D. Double Staining with Ki-67/PKKK1 (Confirmation of Trophoblast Cell Type): Sterile glass coverslips are placed into the wells of a 24-well culture plate (Falcon) and precoated with 500 µl of trophoblast medium or medium containing test compounds. After 24, 48 or 72 hrs of culture, the coverslips are gently washed and fixed with acetone at 4° C. for 5 min. The coverslips are then stained immediately as follows: coverslips are rehydrated in PBS and incubated for 30 min at room temperature with monoclonal antibodies to PKKK1 (in cytoplasm) and Ki-67 (in nucleus)(1/10, Dako) simultaneously. The rest of the staining follows the procedure described in Chegrin et al., in *Growth factors and the overy* (Hirshfield ed.) Plenum Press, New York, p.213–220 (1988).

E. Statistical Analysis: Basal levels of cytokines and eicosanoids are tabulated, and the effects of the different test compounds are assessed by comparing changes in the levels of cytokines and eicosanoids by test compounds. Significance of the differences between mean values of each experiment are evaluated by ANOVA. Data are expressed as mean±standard deviation. A p value<0.05 is considered significant.

F. Results of In Vitro and Ex Vivo Trophoblast Culture Experiments

Since the clinical definition of preeclampsia consists of clinical signs and symptoms in the third trimester of pregnancy, it is impossible to classify trophoblast cells from first or second trimesters as preeclamptic. Therefore, culture experiments with M-CSF and GM-CSF were performed using either spontaneous abortus speciments in the 1st or 2nd trimester or using JEG-3 choriocarcinoma cells as a model of 1st trimester trophoblast cells. In response to 200 U/ml of M-CSF or GM-CSF, proliferation increased (p<0.05) over controls during 72 hours of incubation (Table 1). In 1st trimester trophoblast cells (n=3 spontaneous abortus specimens) proliferation increased in a dose dependent manner (Table 2)

In contrast, third trimester trophoblast cells from normal and preeclamptic pregnancy displayed no response to M-CSF or GM-CSF (Table 3). This would seem consistent with prvious findings in the literature cited in the background section of the application.

Proliferation Results: Trophoblast cells from normal pregnancies survived better than those from preeclamptic pregnancies (Table 1); the difference was most prominent at day 5 of cell culture.

TABLE 1

PROLIFERATION OF JEG-3 CHORIOCARCINOMA CELLS
(MODEL OF 1ST TRIMESTER TROPHOBLAST CELLS)

| | CONTROL | M-CSF (200U/ML) | GM-CSF(200U/ML) |
|---|---|---|---|
| DAY 1 | 100 | 124 ± 10.5 | 120 ± 9.7 |
| DAY 2 | 145 ± 10.3 | 187 ± 15.6 | 203 ± 20.1 |
| DAY 3 | 197 ± 25.9 | 341 ± 37.1 | 337 ± 45.2 |

Data expressed as percent ratio of each value compared to control
(Day 1 without growth factors). % = value (Optical Density) (Day 1) × 100.

TABLE 2

PROLIFERATION OF 1ST TRIMESTER TROPHOBLAST CELLS

| M-CSF (U/ML) | % CHANGE FROM CONTROL |
|---|---|
| 2 | 1.75 ± 4.45 |
| 20 | 11.6 ± 4.3 |
| 200 | 16.3 ± 5.5 |
| 2000 | 23.1 ± 5.6 |

(N = 3 Placentae)

TABLE 3A

SURVIVAL OF NORMAL TROPHOBLAST CELLS

| | CONTROL | M-CSF (2000 U/ML) | GM-CSF(2000 U/ML) |
|---|---|---|---|
| DAY 1 | 100 | 104 ± 13.5 | 95 ± 7.2 |
| DAY 3 | 93 ± 10.7 | 90 ± 12.3 | 96 ± 11.2 |
| DAY 5 | 80 ± 12.8 | 82 ± 16.0 | 80 ± 12.9 |

TABLE 3B

SURVIVAL OF PREECLAMPTIC TROPHOBLAST CELLS

|  | CONTROL | M-CSF (2000 U/ML) | GM-CSF(2000 U/ML) |
| --- | --- | --- | --- |
| DAY 1 | 100 | 97 ± 8.8 | 97 ± 9.0 |
| DAY 3 | 84 ± 6.6 | 87 ± 11.4 | 80 ± 14.4 |
| DAY 5 | 58 ± 13.5 | 60 ± 18.7 | 66 ± 19.1 |

G. Results of Placental Bed Biopsy Evaluation of M-CSF.

To evaluate the relationship between M-CSF expression and preeclamptic placental bed lesions, the distribution of M-CSF was studied inplacental bed biopsies from normal (n=11) and preeclamptic (PE) (n=20) pregnancies. Immunohistochemical staining was performed in formalin or bouin's fixed, paraffin-embedded specimens using monoclonal antibodies for recombinant M-CSF, α-actin (a marker for smooth muscle) and macrophages via a streptavidin peroxidase method. In normal biopsies, the cytotrophoblast and syncytiotrophoblast cells were M-CSF positive. The intramural endovascular trophoblast cells of the uteroplacental arteries (UPA) had faint M-CSF staining and the vessels had no α-actin staining. In areas of myointimal proliferation in UPA, M-CSF positive macrophages and trophoblast cells were present. PE arteries, with atherosis, did not stain for M-CSF but did stain for α-actin. Trophoblast cells were absent from vessel walls, but periarterial cytotrophoblast cells were positive for M-CSF.

EXAMPLE 4

Measurement of Serum M-CSF levels and Correlation With Preeclampsia and/or Gestational Hypertension ("GH")

The serum levels of M-CSF were measured at 16 weeks gestation in 68 women. Twenty two of these patients ultimately developed GH, and 46 patients had normal pregnancies. The mean serum M-CSF levels for the patients later developed GH was significantly lower than the mean for patients with normal pregnancies. For patients who later developed GH or preeclampsia, the mean serum M-CSF level was 455.2±10.5 units/ml compared to a mean serum M-CSF level of 536.1±20.4 units/ml (mean±standard deviation) for patients with normal pregnancy. The p value for this measured difference is p<0.01, and is thus considered to be statistically significant.

Further measurements were taken for the 22 patients who developed GH and 21 of the patients with normal pregnancies. For this matched sets of patients, M-CSF levels were again lower in patients with GH, (455.2±10.5 units/ml v. 530.3±16.5 units/ml, p<0.0001). Serum M-CSF levels were inversely related to maximum diastolic pressure during pregnancy (R=−0.472, p<0.0005) and maximum systolic pressure during pregnancy (R=−0.472, p<0.0001). Of the 22 patients with GH, 6 were diagnosed as preeclamptic. None of the patients without GH was diagnosed as preeclamptic. Four women were diagnosed as suffering from HELLP Syndrome [Hemolysis Elevated Liver enzymes Low Platelets], the most severe manifestation of preeclampsia. All four of these women had serum M-CSF levels below 500 units/ml. FIG. 1 is a diagram of the relationship between serum M-CSF levels measured at 16 weeks gestation and final pregnancy outcome (Δ=patient with GH ("PIH"); ⊙=patient with normal pregnancy).

I claim:

1. A method of treating a patient with increased risk of gestational hypertension or preeclampsia, said method comprising administering an effective amount of M-CSF to raise serum M-CSF to normal levels.

2. The method of claim 1, wherein M-CSF is administered beginning late in the first trimester or during the second trimester of pregnancy.

3. The method of claim 2, where M-CSF is administered during the period beginning at approximately 14 to 16 weeks gestation and ending at approximately 30 weeks gestation.

4. The method of claim 1, wherein M-CSF is administered during the period beginning at about 14 to 16 weeks gestation, and administration continues until measured serum M-CSF levels are within normal levels.

5. The method of claim 1, further comprising administering a therapeutically effective amount of IL-11.

6. The method of claim 5, wherein M-CSF is administered beginning prior to administration of IL-11.

7. The method of claim 6, wherein M-CSF is administered beginning during the first trimester of pregnancy until measured serum M-CSF levels are within normal levels, and IL-11 is administered beginning during the second trimester of pregnancy.

* * * * *